United States Patent [19]
Dolak et al.

[11] Patent Number: 6,033,651
[45] Date of Patent: *Mar. 7, 2000

[54] GEL COSMETIC COMPOSITIONS

[75] Inventors: Terence Martin Dolak, Andover; Fred Nick Hubner, East Brunswick; Vijay Kumar Joshi, Livingston; Charles George Shalotsky, Chatham; Tian Xiang Wang, Edison, all of N.J.; David Martin Kellner, Hollis, N.Y.

[73] Assignee: Revlon Consumer Products Corporation, New York, N.Y.

[ * ] Notice: This patent is subject to a terminal disclaimer.

[21] Appl. No.: 09/215,781

[22] Filed: Dec. 18, 1998

Related U.S. Application Data

[60] Provisional application No. 60/088,713, Jun. 10, 1998.

[51] Int. Cl.$^7$ .............................. A61K 7/32; A61K 9/00; A61K 7/00
[52] U.S. Cl. .......................... 424/65; 424/400; 424/401; 514/937; 514/944
[58] Field of Search ................................. 424/400, 401, 424/65; 514/937, 944

[56] References Cited

U.S. PATENT DOCUMENTS

| | | | |
|---|---|---|---|
| 5,540,853 | 7/1996 | Trinh et al. | 510/101 |
| 5,635,165 | 6/1997 | Panitch | 424/65 |
| 5,645,903 | 7/1997 | Tanaka et al. | 428/34.1 |

FOREIGN PATENT DOCUMENTS

| | | |
|---|---|---|
| 2 013 085A | 8/1979 | United Kingdom . |
| 95/31967 | 11/1995 | WIPO . |

*Primary Examiner*—Shelley A. Dodson
*Assistant Examiner*—Marina Lamm
*Attorney, Agent, or Firm*—Julie Blackburn

[57] ABSTRACT

A single phase aqueous gel composition comprising 0.05–50% of a polysaccharide gellant, and 1–30% of an antiperspirant active ingredient solubilized in the aqueous single phase.

A water and oil emulsion comprising a gelled aqueous phase comprising a polysaccharide gellant and an antiperspirant active ingredient solubilized in the aqueous single phase; and an oil phase.

A method for preparing an emulsion antiperspirant or deodorant composition comprising preparing a first aqueous solution of antiperspirant or deodorant active, preparing a second aqueous solution of polysaccharide gellant, emulsifying the second aqueous solution in an oily phase to form an emulsion, combining the first aqueous solution and the emulsion so that the first and second aqueous solutions form a single homogeneous phase in the emulsion; and pouring the mixture into containers.

19 Claims, No Drawings

GEL COSMETIC COMPOSITIONS

RELATED APPLICATIONS

This application claims the benefit of U.S. Provisional Application No. 60/088,713, filed Jun. 10, 1998.

TECHNICAL FIELD

The invention is the field of solid opaque or clear gel cosmetic compositions which may be in the stick or soft-solid form.

BACKGROUND OF THE INVENTION

Antiperspirants and deodorants are sold in various forms such as gels, solids, roll-ons, and aerosols. Gels are currently popular, since they often are perceived by consumers to have certain advantageous properties such as smooth application and cool, comfortable feel when applied to skin. In addition, when the gels are clear, they are perceived to be cleaner and less apt to stain clothing.

Antiperspirants and deodorants in the gel form are well known in the art. Typically, these gels are in the oil in water emulsion form and contain water and a gellant in addition to other ingredients such as emulsifiers and emollients. Commonly used gellants are dibenzylidene alditols. For example U.S. Pat. No. 4,518,582 teaches acid stable monosorbitol gels which contain a mixture of solvents, dibenzylidene monosorbitol acetal as a gellant, $C_{12-20}$ fatty acids, and a gel stabilizer which is a mixture of magnesium sulfate, zinc acetate, and hexamethylene triamine.

Sodium stearate is also a well known gellant, and is often used in deodorant. For example, PCT WO 97/14398 teaches soap based, clear gel antiperspirant compositions containing 2 methyl 1,3-propanediol. However, sodium stearate tends to react with antiperspirant salts so it is difficult to make sodium stearate based antiperspirant gel compositions.

U.S. Pat. No. 5,587,153 teaches clear gel water in oil emulsion antiperspirant compositions based upon water in silicone emulsions. However, these gels show problems with stability and syneresis.

Agarose and certain other polysaccharides such as gellan gum, carageenans, and the like, are well known gellants and are readily available. However, polysaccharides in general are very unstable in the presence of antiperspirant salts and quickly lose their gelling capabilities when exposed to such salts. Further, including other ingredients in the gel composition to enhance the commercial properties of the gel causes even further instablity, which results in syneresis and other problems which make such products commercially unacceptable.

WO 95/31967 teaches that polysaccharides such carageenans or gellan gum can be used to make antiperspirant gels if the polysaccharide gel is kept removed from the aqueous antiperspirant salt solution via formation of a triple emulsion. In particular, the aqueous antiperspirant salt solution is dispersed in an oil phase. This water in oil emulsion is then dispersed in a gelled aqueous outer phase, which isolates the antiperspirant salt from the gelled phase. This process is disadvantageous because of the preparation of the triple emulsion is tricky and time consuming. In addition, the emulsion itself may not be as stable as desired.

There is a need for an gel composition made from polysaccharides which is stable in the presence of antiperspirant salts, i.e. does not precipitate or exhibit unacceptable levels of syneresis.

An object of the invention is to formulate a single phase gel composition containing polysaccharide gellants.

An object of the invention is to formulate a single phase gel composition containing polysaccharide gellants, which is stable in the presence of antiperspirant salts, i.e. the gel does not precipitate out of the composition and the composition does not exhibit unacceptable levels of syneresis.

Another object of the invention is to prepare a clear or translucent single phase gel composition containing polysaccharides.

Another object of the invention is to prepare an opaque gel composition containing polysaccharides.

Another object of the invention is to prepare a gel composition containing polysaccharide gellants suitable for use as an antiperspirant or deodorant stick or soft solid.

Another object of the invention is to provide a method for making a solid gel antiperspirant/deodorant composition which is stable.

SUMMARY OF THE INVENTION

The invention comprises a single phase aqueous gel composition comprising, by weight of the total composition aqueous gel phase composition:

0.05–50% of a polysaccharide gellant, and

1–30% of an antiperspirant active ingredient solubilized in the aqueous single phase.

A water and oil emulsion solid composition comprising, by weight of the total water and oil emulsion solid composition:

1–85% of a single phase aqueous gel composition comprising a polysaccharide gellant and an antiperspirant active solubilized in the single phase, and 0.1–75% of an oily phase.

The invention comprises a method for making an antiperspirant/deodorant composition comprising the steps of:

(a) preparing a first aqueous solution of antiperspirant/deodorant active, (b) preparing a second aqueous solution of polysaccharide gellant, (c) emulsifying the second aqueous solution in an oily phase to form an emulsion, (d) combining the first aqueous solution and the emulsion wherein the first and second aqueous solutions form a single homogeneous phase in the emulsion; and (d) pouring the mixture into containers.

DETAILED DESCRIPTION

The Single Aqueous Phase Gel Compositions

The gel compositions of the invention are characterized by being single phase, which means that all of the ingredients in the composition, including the antiperspirant salt, exist in the same phase, i.e. the gel composition itself is not the emulsion form, or in the form of a suspension where the particulate antiperspirant salts or other ingredients are suspended or dispersed in the composition. In addition, the antiperspirant active ingredient is solubilized in the aqueous single phase composition as opposed to being found in the suspensoid form in the composition. However, if desired, the single phase composition of the invention can be emulsified or dispersed into an oily phase to create a final composition in the form of a water-in-oil emulsion or oil-in-water emulsion where the water phase comprises the single phase gel composition, which forms either the continuous phase or dispersed phase of the emulsion.

The compositions contain the following ingredients, with all percentages mentioned herein being percentages by weight unless otherwise indicated:

POLYSACCHARIDE GELLANT

The compositions of the invention contain 0.05–50%, preferably 0.1–40%, more preferably 0.5–35% by weight of the total gel composition of a polysaccharide gellant. The term "polysaccharide gellant" means a water soluble compound or composition (i) containing at least one saccharide moiety; and (ii) which, upon mixing with water in a ratio of about 1 to 1 at room temperature (25° C.) is capable of forming either a soft gel having a gel having a viscosity of about 1,000 to 800,000 centipoise at 25° C., and/or a gel strength of about 10 to 5,000 grams/cm$^2$ at 25° C. as measured using a TA.XT2i texture analyzer with a ½ inch diameter cylindrical probe. The term "saccharide moiety" means a polyhydroxy aldehyde or ketone, or acid hydrolysis product thereof, which, preferably, has the general formula $C_x(H_2O)_y$. Examples of saccharide moieties include the D and L forms of glucose, fructose, xylose, arabinose, fucose, galactose, pyruvic acid, succinic acid, acetic acid, galactose, 3,6-anhydro-galactose sulfate, galactose-4-sulfate, galactose-2-sulfate, galactose-2,6-disulfate, mannose, glucuronic acid, mannuronic acid, guluronic acid, galactouronic acid, rhamnose, and so on. Preferably the polysaccharide gellants have a molecular weight ranging from about 500 to 15,000,000 daltons, preferably 5,000 to 1,000,000, more preferably 25,000 to 500,000 daltons. Polysaccharide gellants which fulfill the above criteria include polysaccharides such as galactans, galactomannans, glucomannans, polyuronic acids, and the like. Suitable galactans are agar, agarose, and kappa carageenan, iota carageenan, lambda carageenan. Examples of suitable galactomannans are locust bean gum and guar; examples of glucans are cellulose and derivatives thereof, starch and derivatives, dextrans, pullulan, beta 1,3-glucans, chitin, xanthan, tamarind and the like; examples of glucomannans are konjac; examples of polyuronic acids are algin, alginates, pectins; examples of heteropolysaccharides are gellan, welan, gum arabic, karaya gum, okra gum, aloe gum, gum tragacanth, gum ghatti quinceseed gum, psyllium, starch arabinogalactan and so on.

Preferred are galactans, in particular agarose, which is a polysaccharide comprised of basic repeating units of 1,3-linked beta-D-galactopyranose and 1,4-linked 3,6-anhydro-alpha-L-galactopyranose saccharide moieties. The agarose may be substituted by hydrophobic or hydrophilic groups. Examples of hydrophobic groups are alkoxy, in particular, methoxy. Examples of hydrophilic or polar groups are sulfate, pyruvate and the like. Examples of such substitutions are taught in Aoki, T.T.; Araki & M. Kitamikado; 1990, Vibrio sp. AP-2. *Eur. J. Biochem*, 187, 461–465, which is hereby incorporated by reference. The average molecular weight of agarose ranges between 35,700 and 144,000 daltons. The agarose suitable for use in the compositions of the invention may be from any suitable source or locale. For example an article authored by M. Lahaye and C. Rochas, *Hydrobiologia*, 221, 137–148, 1991, which is hereby incorporated by reference, discusses the numerous different types of agarose from different origins of seaweed species, all of which are suitable for use in the compositions of the invention. Also suitable for use in the compositions of the invention are chemically modified agaroses, such as those taught in an article authored by K. B. Guiseley in *Industrial Polysaccharides:Genetic Engineering, Structure/Property Relations and Applications*, Edited by M. Yalpani, 1987, Elsevier Science Publishers, which is hereby incorporated by reference. The Guiseley article teaches methods for the chemical modification of agaroses to obtain optimum gelling properties. One example of modified agarose is a hydroethylated agarose which is sold under the brand names Sea-Plaque and SeaPrep from FMC, Inc. In general, any modification of agarose which does not affect the helical conformation (i.e. which is obtained via linkage of the O6 and O4 of galactose to the O2 of 3,6-anhydrogalactose) will preserve the gelling capability.

In the most preferred embodiment of the invention, the composition contains at least two polysaccharide gellants, preferably a galactan and one gellant which is a galactomannan, glucan, glucomannan, polyuronic acid, or heteropolysaccharide. Agarose suitable for use in the compositions can be purchased from FMC Inc, under the tradenames Seakem LE and Seakem CLE.

ANTIPERSPIRANT ACTIVE

The compositions of the invention contain 1–30%, preferably 5–25%, more preferably 10–22% by weight of the total single phase aqueous composition of antiperspirant active salt.

The term "antiperspirant active salt" or "antiperspirant salt" means any compound or composition having antiperspirant activity, preferably astringent metallic salts such as the inorganic and organic salts of aluminum, zirconium, and zinc, and mixtures thereof. Particularly preferred are the aluminum and zirconium salts such as aluminum halides, aluminum hydroxide halides, zirconyl oxide halides, zirconyl hydroxy halides, and mixtures thereof. Aluminum salts include those of the formula:

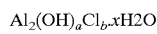
$Al_2(OH)_aCl_b \cdot xH_2O$ wherein a is from about 2 to 5; a+b=6; x is from about 1 to about 6; and wherein a, b, and x may have non-integer values. Zirconium salts include those of the formula:

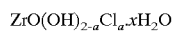
$ZrO(OH)_{2-a}Cl_a \cdot xH_2O$ wherein a is from about 1.5 to about 1.87; x is from about 1 to about 7; and wherein a and n may have non-integer values.

Examples of aluminum and zirconium salts include aluminum chloride, aluminum chlorohydrate, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum zirconium octachlorohdrate, aluminum zirconium octachloroydrex GLY, aluminum zirconium pentachlorohydrate, aluminum zirconium pentachlorohydrex GLY, aluminum zirconium tetrachlorohydrate, aluminum zirconium tetrachlorohydrex GLY, aluminum zirconium trichlorohydrate, aluminum zirconium trichlorohydrex GLY, and mixtures thereof.

Particularly preferred zirconium salts are those complexes also containing aluminum and glycine, in particular, aluminum zirconium tetrachlorohydrex GLY. The antiperspirant salts used in the composition of the invention are solubilized in the water. While preferably the antiperspirant salts are completely dissolved in the water, in some cases small amounts of salts may not be dissolved, i.e. may remain in the crystalline or suspensoid form.

WATER

The single phase aqueous composition of the invention also contains water. Preferably the composition contains 1–90%, more preferably 3–80%, most preferably 5–60% water.

In one preferred embodiment of the invention the composition is clear or translucent, which means that the composition has a refractive index ranging from about 1.0 to 1.6, preferably 1.2 to 1.5 at 21° C. and an optical clarity of less than about 50 Nephelometric turbidity units (NTU) when measured with an Orbeco-Hellige #965 direct reading turbidometer, and a gel strength of 500 to 5000 grams/cm².

OTHER INGREDIENTS

The single phase aqueous compositions of the invention may contain other ingredients which enhance the beneficial properties.

Gel Structure Modifiers

Preferably, the single phase aqueous composition contains 1–50%, preferably 2–40%, more preferably 5–35% of at least on gel structure modifier. The term "gel structure modifier" means an ingredient which is capable of modifying the gel structure in some fashion; for example by plasticizing the gel structure, improving texture or moisturizing properties, which provide the end result of improving payoff; formed by the aqueous polysaccharide gel such that it exhibits improved pay off when applied to the skin. For example, antiperspirant stick or gel compositions, when applied to the skin, must deposit a certain amount of product onto the skin. The amount of material deposited onto the skin as the gel is rubbed across the skin surface is called "pay off". If a gel does not have adequate pay off, when the gel is rubbed across the underarm skin, a sufficient amount of the gel composition will not rub off onto the skin. On the other hand, if the gel has too much pay off, when it is rubbed across the underarm skin too much of the gel deposits on the skin. Thus, it is important to regulate the gel structure and consistency so that pay off is optimal. Generally, suitable gel structure modifiers include polyols, aliphatic short chain mono-, di, and polyhydric alcohols, ethoxylated and/or propoxylated fatty alcohols or glycols, monomer and polymeric ethers and block copolymers, and the like.

1. Polyols

Suitable polyols are defined as compounds which contain three or more hydroxyl groups per molecule. Examples of suitable polyols include fructose, glucamine, glucose, glucose glutamate, glucuronic acid, glycerin, 1,2,6-hexanetriol, hydroxystearyl methylglucamine, inositol, lactose, malitol, mannitol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, riboflavin, sorbeth-6, sorbeth-20, sorbeth-30, sorbeth-40, sorbitol, sucrose, thioglycerin, xylitol, and mixtures thereof.

2. Ethers

Also suitable as gel structure modifiers are homopolymeric or block copolymeric liquid ethers. Polymeric ethers are preferably formed by polymerization of monomeric alkylene oxides, generally ethylene or propylene oxides. Preferred monomeric ethers are those exhibiting the structure below were n=1. Preferred polymeric ethers are comprised of moieties having the general structure below wherein n=2 to 100:

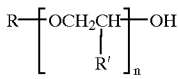

where R and R' are each independently H, or $C_{1-30}$ straight or branched chain alkyl, and n is 1 to 20. Examples of such polymeric ethers include PEG, PPG, PEG/PPG copolymers, and derivatives thereof as well as alkoxylated alcohols such as steareth 2–100, ceteth 2–100, and the like.

Other examples of suitable polymeric ethers include polyoxypropylene polyoxyethylene block copolymers having the general formula:

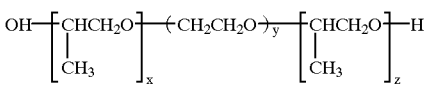

wherein x is 1–200, y is 1–200 and z is 1–200. Such compounds are sold under the CTFA name Meroxapol 105, 108, 171, 172, 174, 178, 251, 252, 254, 255, 258, 311, 312, and 314.

3. Alcohols

Mono- and dihydric alcohols are also suitable for use as gel structure modifiers. Generally, these mono- and dihydric alcohols have the general formula $R(OH)_n$ where n is 1 or 2 and R is a substituted or unsubstituted saturated $C_{2-10}$, preferably $C_{1-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, triethylene glycol, dipropylene glycol, methyl propanediol, and mixtures thereof.

4. Sorbitan Derivatives

Sorbitan derivatives, which are defined as ethers or esters of sorbitan, are also suitable gel structure modifiers. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof.

5. Organosiloxane Emulsifiers

Also suitable as gel structure modifiers are organosiloxane emulsifiers, provided they are at least partially soluble in the aqueous single phase composition. Suitable organosiloxane emulsifiers generally contain at least one lipophilic radical or portion and at least one hydrophilic radical or portion so that a portion of the molecule is soluble in the aqueous phase composition and a portion of the molecule is dispersible in the aqueous phase composition. The polymeric organosiloxane used in the invention is preferably a liquid or semi-solid at 25° C. The polymeric organosiloxane is generally a water-in-oil or oil-in-water type surfactant which is preferably nonionic, having an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof. The $C_{1-40}$ alkyl may be non-interrupted, or interruped by one or more oxygen atoms, a benzene ring, amides, esters, or other functional groups.

The polymeric organosiloxane emulsifier used in the invention may have any of the following general formulas:

$$M_xQ_y,$$

or $$M_xT_y,$$

or $$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D'', x, y, and z are as set forth below, with the proviso that the compound contains at least one hydrophilic radical and at least one lipophilic radical. Examples of emulsifiers used in the compositions of the invention are of the general formula:

$$MD_xD'_yD''_zM$$

wherein the trimethylsiloxy endcap unit is unsubstituted or mono-substituted, wherein one methyl group is substituted with a lipophilic radical or a hydrophilic radical. Examples of such substituted trimethylsiloxy endcap units include $(CH_3)_2HPSiO$, $(CH_3)_2LPSiO$, $(CH_3)_2CH_2HPSiO$, $(CH_3)_2CH_2LPSiO$, wherein HP is a hydrophilic radical and LP is a lipophilic radical. D, D', and D'' are difunctional siloxy units substituted with methyl, hydrogen, a lipophilic radical, a hydrophilic radical or mixtures thereof. In this general formula:

x=0–5000, preferably 1–1000 y=0–5000, preferably 1–1000, and z=0–5000, preferably 0–1000, with the proviso that the compound contains at least one lipophilic radical and at least one hydrophilic radical. Examples of these polymers are disclosed in U.S. Pat. No. 4,698,178, which is hereby incorporated by reference.

Particularly preferred is a linear silicone of the formula:

$$MD_xD'_yD''_zM$$

wherein $M = RRRSiO_{1/2}$
D and $D' = RR'SiO_{2/2}$
$D'' = RRSiO_{2/2}$
x, y, and z are each independently 0–1000,
where R is methyl or hydrogen, and R' is a hydrophilic radical or a lipophilic radical, with the proviso that the compound contains at least one hydrophilic radical and at least one lipophilic radical.

Most preferred is wherein
M = trimethylsiloxy
$D = Si[(CH_3)][(CH_2)_nCH_3]O_{2/2}$ where n=1–40,
$D' = Si[(CH_3)][(CH_2)_o-O-PE)]O_{2/2}$ where PE is $(-C_2H_4O)_a(-C_3H_6O)_bH$, o=0–40,
a=1–100 and b=1–100, and
$D'' = Si(CH_3)_2O_{2/2}$ Typical examples of preferred organosiloxane emulsifiers in accordance with the invention include those set forth below:

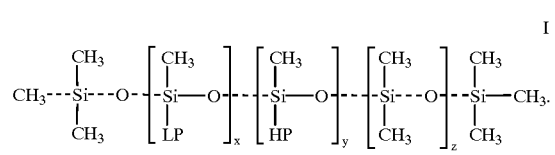

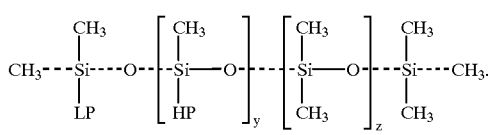

-continued

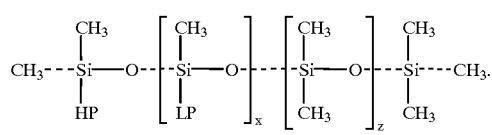
III

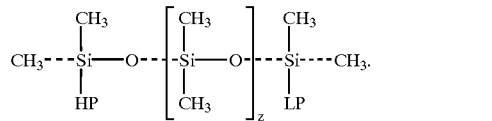
IV

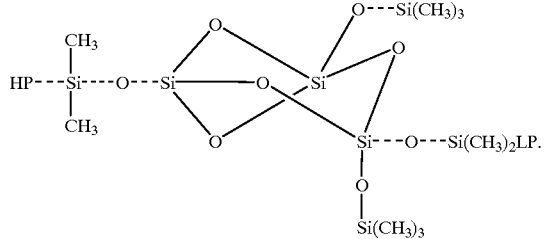
V wherein LP is a lipophilic radical
HP is a hydrophilic radical
x is 0–5000
y is 0–5000, and
z is 0–5000, with the proviso that the organosiloxane contains at least on hydrophilic radical and at least one lipophilic radical.

More preferred are compounds of the generic formula I wherein LP is a lipophilic radical which is a $C_{1-40}$ straight or branched chain alkyl, HP is a hydrophilic radical containing hydroxy-polyethyleneoxy, and z is at least 1. Most preferred is a compound of the formula:

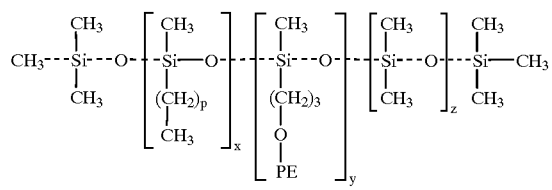

wherein p is 1–40, and
PE is $(-C_2H_4O)_a(-C_3H_6O)_b-H$
where x, y, z, a, and b are such that the molecular weight of the polymer ranges from about 500 to 100,000. Organosiloxane polymers useful in the compositions of the invention are commercially available from Goldschmidt Corporation under the ABIL tradename. The preferred polymer is cetyl dimethicone copolyol and has the tradename ABIL WE 09 or ABIL Ws 08.

Another type of preferred organosiloxane emulsifier suitable for use in the compositions of the invention are emulsifiers sold by Union Carbide under the Silwet™ trademark. These emulsifiers are represented by the following generic formulas:

wherein PE=$-(EO)_m(PO)_nR$
R=lower alkyl or hydrogen
Me=methyl

EO is polyethyleneoxy
PO is polypropyleneoxy
m and n are each independently 1–5000
x and y are each independently 0–5000, and

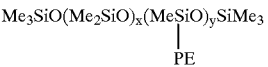

wherein PE=$-CH_2CH_2CH_2O(EO)_m(PO)_nZ$
Z=lower alkyl or hydrogen, and
Me, m, n, x, y, EO and PO are as described above,
with the proviso that the molecule contains a lipophilic portion and a hydrophilic portion. Again, the lipophilic portion can be supplied by a sufficient number of methyl groups on the polymer backbone.

Particularly preferred is a Silwet™ polymer of the following general formula:

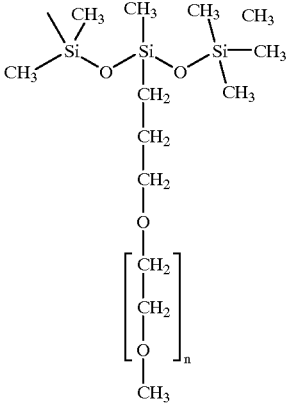

Wherein n is 1–10, preferably 8.

Another preferred organosiloxane emulsifier for use in the compositions of the invention is dimethicone copolyol. Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane emulsifiers sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

Preferred is where the gel structure modifier is selected from a monomeric ether, polymeric ether, monohydric alcohol, dihydric alcohol, organosiloxane emulsifier, polymeric ether, or mixtures thereof. Particularly preferred is wherein the monohydric alcohol is a $C_{2-10}$ alkanol, preferably ethanol, and the dihydric alcohols are of the formula ROR' wherein each R and R' are independently H or a $C_{2-10}$ unsubstituted or substituted alkyl, where the substituent is hydroxyl or methyl; such compounds being preferably propylene glycol, dipropylene glycol, and methyl propandiol.

Deodorant Actives

It may be desired to incorporate into the cosmetic gel composition one or more deodorant actives. If so, a range of about 0.1–30% of deodorant active is suggested. The deodorant actives should be soluble in the aqueous single phase composition, or water dispersible carrier, such as triclosan encapsulated in cyclodextrin, which may be purchased from Lipo, Inc. Examples of suitable deodorant actives include fragrances, ammonium phenolsulfonate, benzalkonium chloride, benzethonium chloride, bromochlorophene, cetylpyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarbone, triclosan, zinc phenolsulfonate, zinc ricinoleate, and mixtures thereof. The preferred deodorant active is triclosan, fragrance and the like.

The composition of the invention may contain other ingredients, providing such ingredients are soluble in the aqueous single phase composition, or water dispersible/miscible via emulsification or a delivery system. Such ingredients may possibly include humectants, detackifiers such as dimethyl isosorbide, preservatives, surfactants, and so on.

In preparing the single aqueous phase composition, it may be desireable to prepare the composition by combining all ingredients together and mixing well, preferably with elevated temperature. It may also be desired to prepare separate phases of the single aqueous phase composition as a pre-mix, and then combine the separate pre-mixes together. For example, it is believed that the final composition exhibits improved stability when the single aqueous phase is prepared as two pre-mixes. The first pre-mix is an aqueous solution of antiperspirant salt. The second pre-mix comprises water, and the desired water soluble ingredients as mentioned above. The first and second pre-mix are then combined and mixed well to provide the single aqueous phase composition.

Water and Oil Emulsion Solid Compositions

As noted, the single phase aqueous gel composition of the invention may be used alone, or it may be used to form an emulsion. In the latter case, the gel composition may either be dispersed into an oily phase, or the gel composition may form the continuous phase and the oily phase may be dispersed into the gel composition. The oily phase should be insoluble or immiscible with the aqueous gel phase. If the gel composition is used to form an emulsion, generally the emulsion composition will contain about 1–85%, preferably 5–70%, more preferably 7–60% by weight of the total emulsion composition of the aqueous single phase gel composition, and about 0.1–75%, preferably 0.5–65%, more preferably 1–50% by weight of the total emulsion composition of oil. Preferably, the emulsions are oil in water emulsions.

OILS

The oils used may be volatile or nonvolatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C. Suitable volatile solvents generally have a viscosity of 0.5 to 10 centistokes at 25° C. Suitable volatile oils include linear silicones, cyclic silicones, paraffinic hydrocarbons, or mixtures thereof.

Cyclic silicones (or cyclomethicones) are of the general formula:

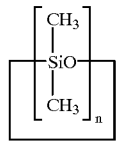

where n=3–7.

Linear volatile silicones in accordance with the invention have the general formula:

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic ydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

A wide variety of nonvolatile oils are also suitable for use in the cosmetic compositions of the invention. The nonvolatile oils generally have a viscosity of greater than 10 centipoise at 25° C., and may range in viscosity up to 1,000,000 centipoise at 25° C. Examples of nonvolatile oils suitable for use in the cosmetic sticks of the invention include esters of the formula RCO-OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the *C.T.F.A. Cosmetic Ingredient Handbook*, First Edition, 1988, which is hereby incorporated by reference.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Nonvolatile silicones, both water soluble and water insoluble, are also suitable as the oil component. Such silicones preferably have a viscosity of 10 to 600,000 centistokes, preferably 20 to 100,000 centistokes at 25° C. Suitable water insoluble silicones include amodimethicone, bisphenylhexamethicone, dimethicone, hexadecyl methicone, methicone, phenyl trimethicone, simethicone, dimethylhydrogensiloxane, stearoxytrimethylsilane, vinyldimethicone, and mixtures thereof.

Also suitable as the nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

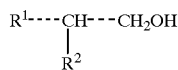

with a carboxylic acid having the general formula:

$R^3COOH$, or $HOOC—R^3—COOH$ wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

Preferably, the guerbet ester is a fluoro-guerbet ester which is formned by the reaction of a guerbet alcohol and carboxylic acid (as defined above), and a fluoroalcohol having the following general formula:

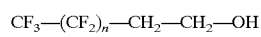

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech, Norcross Georgia as Developmental Ester L61125A, under the tradename Silube GME-F.

Preferably, the compositions of the invention contain a mixture of volatile and nonvolatile silicone oils, so that the amount of volatile oil is about 1–10%, by weight of the total composition, and the amount of nonvolatile oil is about 1–10% by weight of the total emulsion composition. In the preferred embodiment of the invention, the preferred volatile oil is cyclomethicone and the preferred nonvolatile oil is a low viscosity dimethicone. i.e dimethicone having a viscosity of about 5–25 centipoise at 25° C.

WAXES

The oily phase of the emulsion may contain one or more materials that are solid at room temperature such as fatty acids, fatty alcohols, and the like. These materials act as gel structure modifiers for the oily phase. Suggested ranges of oily phase gel structure modifiers are 0.1–30%, preferably 0.5–25%, more preferably 1–20% by weight of the total emulsion composition. Suitable oily phase gel structure modifiers include straight or branched chain fatty alcohols having the formula R—OH, wherein R is a straight or branched chain saturated or unsaturated alkyl having 6–30 carbon atoms. Such fatty alcohols include cetyl alcohol, stearyl alcohol, cetearyl alcohol, and the like. Also suitable are fatty acids having the formula R—COOH, wherein R is a straight or branched chain saturated or unsaturated alkyl having 6–30 carbon atoms, which may be substituted with one or more hydroxyl groups. Preferred are fatty acids wherein R is straight or branched chain alkyl have 12–22 carbon atoms, which may be substituted with one or more hydroxyl groups. Particularly preferred is 12-hydroxystearic acid.

If the aqueous gel composition is combined with an oil phase to form an emulsion, the compositions prepared may be opaque, or clear or translucent. If clear, translucent compositions are desired, the oils selected should not be hazy or cloudy in appearance. Clarity is then achieved by matching the refractive indices of both phases such that they match within about 0.0001 to 0.0006.

An emulsion composition may be formed by preparing the single aqueous phase composition and emulsifying it into the oily phase. It may also be desired to prepare the single aqueous phase in one or more pre-mix phases. One pre-mix is emulsified into the oily phase. The second pre-mix is then emulsified into the emulsion to form a stable emulsion of the two combined pre-mixes which form a single aqueous phase, which is emulsified into the oily phase, as further described below.

The Method

The invention comprises a method for making an antiperspirant or deodorant composition comprising the steps of:

(a) preparing a first aqueous solution comprised of an antiperspirant or deodorant active, (b) preparing a second aqueous solution comprised of a polysaccharide gellant, (c) emulsifying the second aqueous solution in an oily phase to form an emulsion, (d) combining the first aqueous solution and the emulsion so that the first and second aqueous solutions form a single homogeneous phase in the emulsion; and (d) pouring the mixture into containers.

The first aqueous solution (or pre-mix) is prepared by mixing the desired antiperspirant or deodorant active, preferably antiperspirant active, with water until the active has dissolved in the water. If a deodorant active is used, the deodorant actives mentioned herein are suitable, and in the ranges stated. The aqueous solution of active in water may be prepared or purchased in the solution form. Generally, the aqueous active solution comprises about 10–85%, preferably 15–65% by weight of the total aqueous solution of antiperspirant active. Most preferred is an aqueous antiperspirant active solution containing about 43% by weight of the total first aqueous solution of dissolved antiperspirant salt. If desired, other water soluble ingredients may be incorporated into the first aqueous solution, such as those referred to as gel structure modifiers herein, and in the amounts set forth, are suitable. Particularly suitable are silicone surfactants, polyols, and the like. If so, suggested ranges of ingredients include 0.1–50% by weight of the total first aqueous solution of silicone surfactant is suggested, and 5–95% by weight of the total first aqueous solution of polyol is suggested. It may also be desired to include bases such as acetamide MEA or similar materials for pH adjustment.

The second aqueous solution (or pre-mix) is prepared by dissolving a polysaccharide gellant in water. Suitable polysaccharide gellants are as mentioned herein. Generally, the polysaccharide gellant comprises about 1–50% by weight of the total second aqueous solution, and water comprises about 50–99% by weight of the total second aqueous solution. If desired, other ingredients such as silicone surfactants, polyols, and other water soluble ingredients may be added to the second aqueous solution. In general, the water soluble ingredients may be added to either the first or second aqueous phase solution. Suitable ingredients are those set forth under "Gel Structure Modifiers" as set forth herein, and in the ranges specified. Preferably, the other water soluble ingredients are added to the second aqueous phase solution, and include silicone surfactants, polyols, and certain bases, including acetamide MEA, which adjust the composition to the approapriate pH. Preferably the second aqueous phase solution is prepared by heating the water and other water soluble ingredients to a temperature of about 100 to 105° C. The polysaccharide gellant is added to the water and mixed well until the gellant is dissolved and the solution is clear. The temperature is then reduced slightly, to about 85–90° C.

Then, the second aqueous phase solution is emulsified into an oily phase. Generally, the oily phase ingredients are pre-mixed. Suitable oily phase ingredients are as set forth herein, in the ranges given. The oily phase ingredients are then mixed with the second aqueous phase solution at slightly elevated temperature, preferably about 65 to 85° C. The second aqueous phase solution and oily phase are mixed well to form an emulsion.

Then the first aqueous solution is added to the emulsion formed when combining the second aqueous solution and the oily phase. The first and second aqueous solutions become one single homogeneous phase in the emulsion. Preferably the single homogeneous phase formed by the combination of first and second aqueous solutions is the continuous phase of the emulsion and the oily phase is the dispersed phase, thus providing an oil-in-water emulsion. However, the emulsion formed may be a water-in-oil emulsion as well. Preferably, the first aqueous solution is eated to a temperature of about 50 to 65° C. prior to mixing it with the emulsion. It is preferable that the emulsion be maintained at a temperature of 50 to 75° C., preferably 60 to 75° C. when mixing with the first aqueous solution. Generally about 20–80 parts of the emulsion are mixed with about 20 to 80 parts of the first aqueous solution. More preferably the composition is made by mixing about 45–65 parts of the first aqueous solution with 35 to 65 parts of the emulsion. Most preferred is where 58 parts of the first aqueous solution is mixed with 42 parts of the emulsion. The emulsion and first aqueous solution are mixed well and poured into the desired containers, preferably at a temperature of about 55 to 70° C.

The method of the invention provides an antiperspirant or deodorant stick which exhibits improved long term stability.

The invention will be further described in connection with the following examples which are set forth for the purposes of illustration only.

EXAMPLE 1

A single phase clear gel antiperspirant composition was made according to the following formula:

|  | w/w % |
|---|---|
| Aluminum zirconium tetrachlorohydrex gly (35% aqueous solution) | 60.00 |
| Butylene glycol | 20.00 |
| Water | 20.00 |
| Seakem LE Agarose | 1.00 |

The composition was made by adding all of the ingredients together and mixing well. The mixture was heated to 80° C. and then cooled and allowed to gel.

EXAMPLE 2

A single phase clear antiperspirant composition was made according to the following formula:

|  | w/w % |
|---|---|
| Aluminum zirconium tetrachlorohydrex gly (35% aqueous solution) | 60 |
| Seakem LB Agarose | 1.0 |
| Water | QS |

The ingredients were mixed together and heated to 80° C. with stirring to mix well. The composition was allowed to cool and formed a translucent gel having a gel strength of about 500 grams/cm$^2$.

EXAMPLE 3

Oil in water emulsion antiperspirant compositions were made according to the following formulas:

EXAMPLE 3

Oil in water emulsion antiperspirant compositions were made according to the following formulas:

| | w/w % | | | | | | | | |
|---|---|---|---|---|---|---|---|---|---|
| | 1 | 2 | 3 | 4 | 5 | 6 | 7 | 8 | 9 |
| Agarose | 1.00 | 1.20 | 1.00 | 2.00 | 1.00 | 1.00 | 4.00 | 1.00 | 1.00 |
| Al/Zr tetrachlorohydrexGLY PG (30% propylene glycol soln) | — | — | — | — | — | — | 75.00 | — | — |
| Al/Zr tetrachlorohydrexGly (43%) | — | — | — | — | 58.00 | 58.00 | — | 58.00 | 58.00 |
| Al/Zr tetrachlorohydrexGly (35%) | 68.00 | 68.00 | 68.00 | 68.00 | — | — | — | — | — |
| Water | 31.00 | 27.80 | — | 18.00 | 21.00 | 29.00 | — | 12.00 | 14.00 |
| Propylene glycol | — | 10.00 | 15.00 | — | — | — | — | — | — |
| Ethanol | — | — | 5.00 | — | — | — | — | — | — |
| Dimethicone copolyol | — | — | — | 2.00 | — | — | — | — | — |
| Dipropylene glycol | — | — | — | 10.00 | 10.00 | 10.00 | — | — | — |
| PEG/PPG-17/6 Copolymer polyalkylene glycol | — | — | — | — | 2.00 | — | — | — | — |
| Water soluble fragrance | — | — | — | — | 0.30 | — | — | — | — |
| Benzethonium chloride | — | — | — | — | 0.10 | — | — | — | — |
| Dimethyl isosorbide | — | — | — | — | — | 2.00 | — | — | — |
| Methyl propane diol | — | — | — | — | — | — | 21.00 | 15.00 | 10.00 |
| Cyclomethicone/dimethicone copolyol | — | — | — | — | — | — | — | 8.00 | — |
| Dimethicone | — | — | — | — | — | — | — | 6.00 | 15.00 |
| Polyoxyethylene (20) soritan monolaurate | | | | | | | | | 2.00 |

The formula 1–7 compositions were made by combining the ingredients and mixing well. The mixtures were heated to a temperature where the polysaccharide solution became clear, and the mixture stirred well. The mixtures were then cooled to room temperature to form a gel.

The Formula 8 composition was made by mixing the antiperspirant salt, agarose, and water and heating the mixture to 80° C. with stirring. Separately, the cyclomethicone/ dimethicone copolyol and dimethicone were mixed well. The antiperspirant salt, agarose, and water mixture was cooled to 40° C. and added slowly with turbulent mixing to the cyclomethicone/dimethicone copolyol and dimethicone mixture to form an emulsion of the aqueous phase polysaccharide mixture in the oil phase mixture. The resulting composition was a clear gel water in oil emulsion.

The Formula 9 composition was made by mixing the antiperspirant salt, agarose, polyoxyethylene (20) sorbitan monolaurate, and water and heating to 80° C. with stirring. The mixture was then cooled to 40° C. The dimethicone was added slowly with vigorous mixing to the water phase mixture to form an oil in water emulsion. The resulting Formula 9 composition was a clear gel oil in water emulsion.

EXAMPLE 4

Antipersipirant stick compositions having capacity were prepared according to the following formulas:

| | w/w % | | | |
|---|---|---|---|---|
| | 1 | 2 | 3 | 4 |
| Dimethicone copolyol | 2.00 | 4.00 | — | — |
| Cyclomethicone and dimethicone cross-polymer | 2.00 | — | — | — |
| Dipropylene glycol | 9.00 | 10.00 | 8.00 | 7.00 |
| 12-hydroxystearic acid | 5.00 | 5.00 | 5.00 | 5.00 |
| Al/Zr tetrachlorohydrex gly (43% aqueous sol.) | 58.00 | 58.00 | 58.00 | 58.00 |
| Acetamide MBA (70% aqueous sol.) | 1.00 | 1.00 | 1.00 | 1.00 |
| Agarose | 1.00 | 1.00 | 1.00 | 1.00 |

EXAMPLE 4-continued

Antipersipirant stick compositions having capacity were prepared according to the following formulas:

| | w/w % | | | |
|---|---|---|---|---|
| | 1 | 2 | 3 | 4 |
| Water | QS | QS | QS | QS |
| Dipropylene glycol dibenzoate | — | — | 6.00 | — |
| Isosteareth-2 | — | — | — | 5.50 |
| Phenyl trimethicone | — | — | — | 0.5 |

The compositions were made by mixing the agarose, dipropylene glycol, and water and heating the mixture to 100 to 105° C. with stirring until the composition was clear with no particulates remaining. The mixture was then cooled to 85 to 90° C. and the 12-hydroxystearic acid added. When all the material was completely melted and the mixture was uniform, then the temperature was reduced to 70 to 75° C. Separately, the silicones, organic surfactants, other ingredients were combined and mixed well and added to the cooled mixture. The acetamide MEA and/or dipropylene glycol dibenzoate was then added to the mixture, which was then maintained at a temperature of 60 to 75° C. The aqueous antiperspirant salt solution was heated to a temperature of 50 to 65° C. and combined with the emulsion mixture with stirring. The resulting compositions were maintained at a temperature of 55 to 70° C. and poured into stick molds to provide opaque gel oil-in-water emulsions which hardened into solid sticks.

While the invention has been described in connection with the preferred embodiment, it is not intended to limit the scope of the invention to the particular form set forth, but, on the contrary, it is intended to cover such alternatives, modifications and equivalents as may be included within the spirit and scope of the invention as defined by the appended claims.

We claim:

1. A water and oil emulsion solid composition comprising a single gelled aqueous phase comprising a polysaccharide gellant selected from the group consisting of galactan, galactomannan, and mixtures thereof, and an antiperspirant active ingredient solubilized in the aqueous single phase; and an oil phase.

2. The composition of claim 1 wherein the emulsion is an oil in water emulsion.

3. The composition of claim 2 wherein the solid emulsion composition comprises, by weight of the total emulsion composition:

1–85% of a single phase aqueous gel composition comprising a polysaccharide gellant selected from the group consisting of galactan, galactomannan, and mixtures thereof, and an antiperspirant active solubilized in the single phase, and 0.1–75% of an oily phase.

4. The composition of claim 3 wherein the oily phase comprises at least one oil and at least one wax.

5. The composition of claim 4 wherein the oil is selected from the group consisting of a volatile silicone, a non-volatile silicone, and mixtures thereof.

6. A method for making an antiperspirant or deodorant composition comprising the steps of:

(a) preparing a first aqueous solution of antiperspirant or deodorant active, (b) preparing a second aqueous solution comprised of a polysaccharide gellant, (c) emulsifying the second aqueous solution in an oily phase to form an emulsion, (d) combining the first aqueous solution and the emulsion so that the first and second aqueous solutions form a single homogeneous phase in the emulsion; and (d) pouring the mixture into containers.

7. The method of claim 6 wherein the first aqueous solution contains an antiperspirant active.

8. The method of claim 6 wherein the second aqueous solution further comprises one or more gel structure modifiers.

9. The composition of claim 1 wherein the polysaccharide gellant has a molecular weight of about 10,000 to 1,500,000 daltons.

10. The composition of claim 9 wherein the polysaccharide gellant is a galactomannan.

11. The composition of claim 9 wherein the polysaccharide gellant is a galactan.

12. The composition of claim 11 wherein the galactan is agar, agarose, carageenan, or mixtures thereof.

13. The composition of claim 12 wherein the galactan is agarose.

14. The composition of claim 1 wherein the antiperspirant salt is an inorganic or organic salt of aluminum, zirconium, or zinc.

15. The composition of claim 1 comprising 1–90% by weight of the total composition of water.

16. The composition of claim 1 further comprising 0.1–20% of a gel structure modifier.

17. The composition of claim 16 wherein the gel structure modifier is selected from the group consisting of a monomeric ether, polymeric ether, monohydric alcohol, dihydric alcohol, organosiloxane emulsifier, and mixtures thereof.

18. The composition of claim 17 wherein the gel structure modifier is a $C_{2-10}$ monohydric alcohol, a dihydric alcohol, or mixtures thereof.

19. The composition of claim 18 wherein the gel structure modifier is a monohydric alcohol selected from the group consisting of ethanol, isopropanol, hexyldecanol, benzyl alcohol, propyl alcohol, and mixtures thereof.

* * * * *